US012765842B2

(12) United States Patent
Franck

(10) Patent No.: US 12,765,842 B2
(45) Date of Patent: Oct. 20, 2026

(54) PHYSIOLOGICAL MEASUREMENT DEVICE, METHOD AND PROGRAM

(71) Applicant: KONINKLIJKE PHILIPS N.V., Eindhoven (NL)

(72) Inventor: Christoph Florian Franck, Magstadt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 277 days.

(21) Appl. No.: 18/572,909

(22) PCT Filed: Jun. 27, 2022

(86) PCT No.: PCT/EP2022/067505
§ 371 (c)(1),
(2) Date: Dec. 21, 2023

(87) PCT Pub. No.: WO2023/274921
PCT Pub. Date: Jan. 5, 2023

(65) Prior Publication Data

US 2024/0225555 A1 Jul. 11, 2024

(30) Foreign Application Priority Data

Jun. 29, 2021 (EP) .................................... 21182420

(51) Int. Cl.
*A61B 5/00* (2006.01)

(52) U.S. Cl.
CPC ............ *A61B 5/7225* (2013.01); *A61B 5/746* (2013.01)

(58) Field of Classification Search
CPC ......... A61B 5/276; A61B 5/30; A61B 5/6843; A61B 5/7221; A61B 5/7225; A61B 5/746
See application file for complete search history.

(56) References Cited

U.S. PATENT DOCUMENTS 8,649,744 B2 2/2014 Acimovic
9,737,265 B2 8/2017 Zheng
(Continued)

FOREIGN PATENT DOCUMENTS

CN 111714112 A 9/2020
JP 2020130875 A 8/2020
(Continued)

OTHER PUBLICATIONS

International Search Report Dated Oct. 26, 2022 for International Appln. No. PCT/EP2022/067505 Filed Jun. 27, 2022.

*Primary Examiner* — Jon Eric C Morales
(74) *Attorney, Agent, or Firm* — Brynne J. Corcoran

(57) ABSTRACT

The present invention relates to a physiological measurement device (11) comprising a processor (37) configured to input (47, 49) at least one digital signal (x) from frontend circuitry (17) of the measurement device (13), the digital signal (x) representing an analog signal (s) present at an input (13) of the frontend circuitry (17) and at least one filtered digital signal (y), the filtered digital signal (y) generated by at least one digital filter (27) from the digital signal (x) based on a set of filter coefficients ($f_k$). In order to allow for implementing alarm-related monitoring efficiently in terms of cost and power consumption so that interference with other measurements devices applied to the same patient is minimized, it is proposed that the measurement device (11) comprise a coefficient calculator (31) configured to perform an adaptation operation (51) based on the digital signal (x) and the filtered digital signal (y); and a checker (33) configured to determine (53) alarm information (A) from a result ($f_k$, $g_1$) of the adaptation operation (51).

11 Claims, 6 Drawing Sheets

(56) References Cited

U.S. PATENT DOCUMENTS

| | | | | |
|---|---|---|---|---|
| 2006/0025824 | A1* | 2/2006 | Freeman | A61B 5/7264 600/518 |
| 2011/0144460 | A1 | 6/2011 | Oh | |
| 2012/0323132 | A1 | 12/2012 | Warner | |
| 2014/0066795 | A1 | 3/2014 | Ferdosi | |
| 2015/0320360 | A1 | 11/2015 | Stetson | |
| 2016/0317096 | A1 | 11/2016 | Adams | |

FOREIGN PATENT DOCUMENTS

| | | | |
|---|---|---|---|
| WO | 2018162365 | A1 | 9/2013 |
| WO | WO2018055969 | A1 | 3/2018 |

* cited by examiner

PHYSIOLOGICAL MEASUREMENT DEVICE, METHOD AND PROGRAM

CROSS-REFERENCE TO PRIOR APPLICATIONS

This application is the U.S. National Phase application under 35 U.S.C. § 371 of International Application No. PCT/EP2022/067505, filed on Jun. 27, 2022, which claims the benefit of International application Ser. No. 21/182,420.6 filed on Jun. 29, 2021. These applications are hereby incorporated by reference herein.

FIELD OF THE INVENTION

The present invention relates to a physiological measurement device comprising a processor configured to input at least one digital signal from frontend circuitry of the measurement device, the digital signal representing an analog signal present at an input of the frontend circuitry and at least one filtered digital signal, the filtered digital signal generated by at least one digital filter from the digital signal based on a set of filter coefficients.

BACKGROUND OF THE INVENTION

An example of the above-mentioned type of measurement devices having a frontend including a digital filter is described in WO 2018/162365 A1. The measurement device described therein can be calibrated by determining a set of filter coefficients of the digital filter based on analog test signals applied to input channels of the measurement device.

SUMMARY OF THE INVENTION

While in operation, physiological measurement devices should monitor certain technical aspects of the measurement process and alert a user if certain problems occur, such as defects of the device, the cables, or the sensors/transducers, the presence of significant interference, or if the connection between sensor/transducer and the patient of poor quality or lost.

Moreover, it is desirable to provide this monitoring for alarm detection and processing in a cost-efficient way, i.e. with low overhead in terms of additional circuitry and computing power needed to implement the monitoring.

Finally, the monitoring should not involve injection of auxiliary currents into the patient's body (e.g. for active impedance measurements to determine the contact quality of adhesive electrodes) even when limiting the currents according to applicable technical standards. Even when a measurement device complies with the standards, there is a risk of undesired interaction between different devices if they are used to monitor the same patient at the same time. The generation of the auxiliary currents also increases to the power consumption of the device, which may be a factor in battery-powered measurement devices.

It is thus an object of the present invention to provide a measurement device, method and computer program that allow for implementing the alarm-related monitoring efficiently in terms of cost and power consumption while minimizing interference with other measurements devices applied to the same patient.

In a first aspect of the present invention a physiological measurement device is presented, the device comprising a processor configured to input at least one digital signal from frontend circuitry of the measurement device, the digital signal representing an analog signal present at an input of the frontend circuitry and at least one filtered digital signal, the filtered digital signal being generated by at least one digital filter from the digital signal based on a set of filter coefficients; a coefficient calculator configured to perform an adaptation operation based on the digital signal and the filtered digital signal; and a checker configured to determine alarm information from a result of the adaptation operation.

The inventor has realized that the results of the adaptation operation needed for implementing an adaptive filter can be exploited for the alarm-related monitoring. As a consequence, little additional effort is needed to provide the alarm-related monitoring. Moreover, special analog monitoring circuitry, e.g. for impedance measurement by auxiliary current injection, is avoided. As a consequence, cost and power consumption of the measurement device are low. Due to the lack of injected auxiliary currents, interference with other measurement devices is minimized.

The result of the adaptation operation may include an updated set of filter coefficients and determining the alarm information may be based on the updated set of filter coefficients. Although any information included in the result of the adaptation operation can be used, the use of the filter coefficients allows to detect alarm conditions effectively because the adapted filter coefficients reflect properties of the analog signal applied to the measurement device.

Preferably, the checker is a constraint checker operating based on at least one constraint defined for at least one variable of the adaptation results. That is, determining the alarm information may be based on at least one alarm constraint applicable to at least one filter coefficient of the set of filter coefficients.

In an example, the adaptation operation is subject to at least one value constraint related to a filter coefficient and the alarm constraint is a subset of the value constraint. A constraint defines a set of values that certain variables, e.g. filter coefficients, are allowed to reach. For sake of simplicity, a constraint and the respective set defined by this constraint will herein be considered as synonyms. A value constraint is considered by the adaptation operation to make sure that certain variables, e.g. filter coefficients, are within reasonable range, e.g. to ensure the digital filter functioning properly. Determining the alarm information may comprise checking at least one alarm constraint against the result of the adaption operation.

Different types of alarms may exist. The alarm types may include “electrode quality low”, “electrode off”, “interference”, “defective cable”, and/or “defective device”. To allow for detecting and processing alarms of multiple different type, it is proposed that the alarm information comprise multiple alarm information elements related to different alarm types, a specific alarm constraint being assigned to each of these alarm information elements.

An alarm type may be of a predefined class. One class corresponds to technical alarms. Technical alarms include alarm or failure conditions related to technical or physical aspects of a measurement process carried out by the measurement device and are triggered if problems occur, such as an internal defect of the measurement device, defective cables connected to the input, defective electrodes sensors or transducers, the presence of significant interference, or poor or lost connection between the input and the respective electrode/sensor transducer. Another class corresponds to application-specific alarms. Application-specific alarms refer to a predefined condition of a physiological parameter or process measured by the measurement device. Accordingly, in certain implementations, the alarm type includes a technical alarm and/or an application specific alarm.

In another implementation, determining the alarm information is based on at least one group of alarm constraints, the alarm constraints of the group of alarm constraints being associated with different severity levels of a certain type of alarm. When defining a group of more than one alarm constraints for a certain alarm type, the respective alarm information element comprises more than two different discrete values corresponding to the different severity levels related to that alarm type.

To allow for simple and reliable determination of the severity levels in a exemplary implementation, the alarm constraints of the group of alarm constraint are sortable so that, starting from a first alarm constraint of the group, each subsequent alarm constraint of a certain alarm constraint of the group is a superset of that certain alarm constraint, the subsequent alarm constraint corresponding to a higher severity level than the certain alarm constraint.

Although the principles of the present disclosure can advantageously applied to a single channel measurement device configured to process one analog signal, many practical applications, in particular ECG or EEG, are based on multi-channel devices configured to process multiple analog signals (e.g. originating from ECG or EEG electrodes). In such multi-channel applications, the result of the adaptation operation comprises a plurality of sets of filter coefficients related to multiple digital filters and multiple alarm constraints, each of the alarm constraints applicable to a different set of the plurality of sets of filter coefficients. Checking the multiple constraints related to multiple different results of adaption operations simultaneously is also referred to as a joint constraint check.

Although the present disclosure is not to a certain type of method used to carry out the adaptation operation, is it preferred that performing the adaptation operation comprises solving an optimization problem. The properties of the digital filter can then be defined based on metrics to be maximized or minimized and on the value constraints.

In a further aspect of the present invention a method for operating a physiological measurement device is presented, the method comprising inputting at least one digital signal from frontend circuitry of the measurement device, the digital signal representing an analog signal present at an input of the frontend circuitry; inputting at least one filtered digital signal generated by at least one digital filter from the digital signal based on a set of filter coefficients; performing an adaptation operation based on the digital signal and the filtered digital signal; and determining alarm information from a result of the adaptation operation.

In yet further aspects of the present invention, there is provided a corresponding computer program which comprises program code means for causing a computer to perform the steps of a method disclosed herein, in particular the method for operating a physiological measurement device, when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method, system, computer program and medium have similar and/or identical preferred embodiments as the claimed system, in particular as defined in the dependent claims and as disclosed herein.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
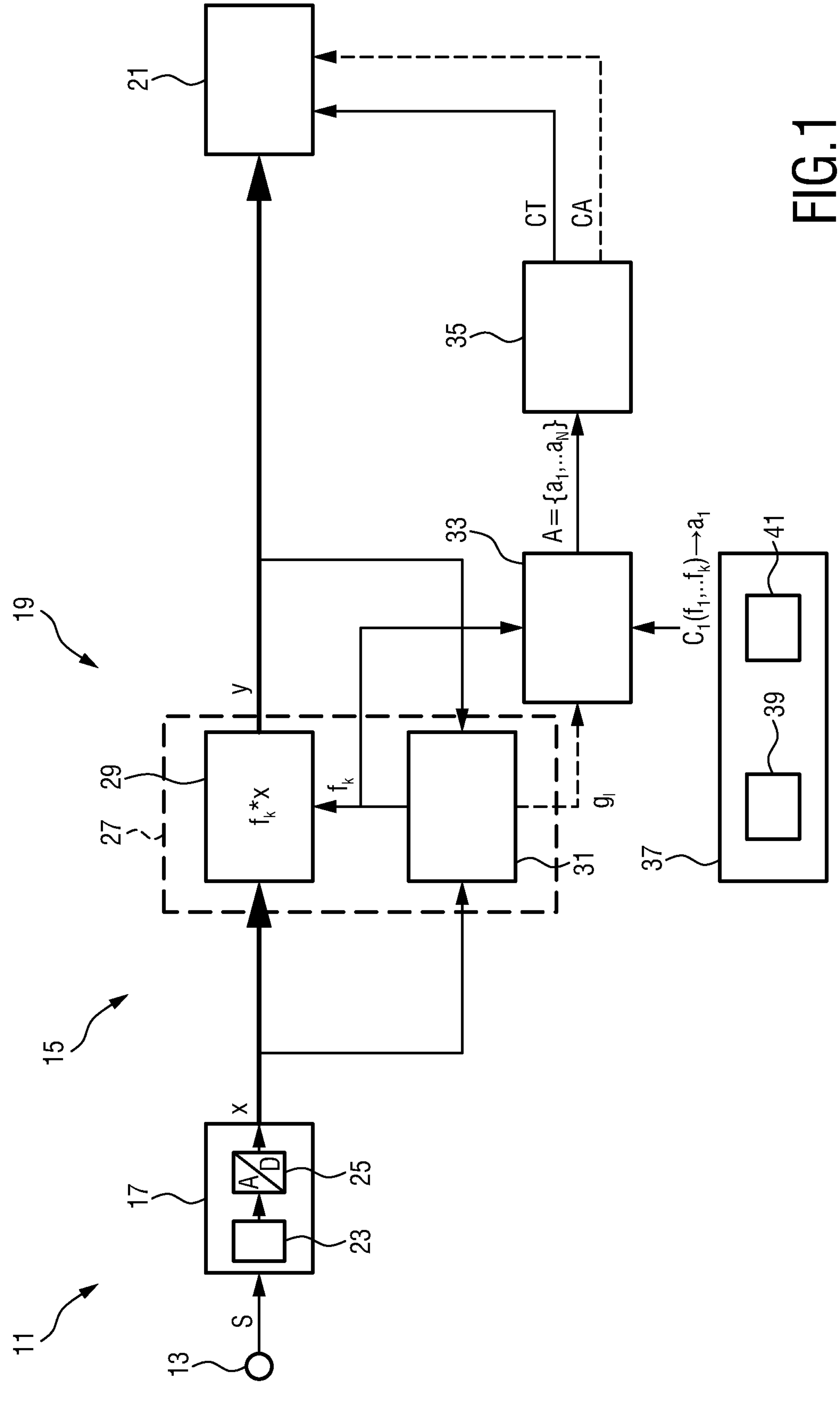
FIG. 1 shows a block diagram of a physiological measurement device.

FIG. 1 shows a block diagram of a physiological measurement device 11. The present disclosure is not limited to a certain type of physiological or medical measurement device. Device 11 may be a patient monitor, maternal/fetal monitor, an electroanatomical imaging system. Moreover, the measurement device may also be a consumer-grade device like smart watch or a fitness tracker with capabilities for monitoring a physiological parameter such as an electrocardiogram (ECG) curve.

Basically, the measurement device 11 comprises an input 13 for inputting an analog electrical signal s representing the physiological parameter to be measured by the device 11. When operating the device 11, the input 13 is typically connected to an electrode applied to a human's or patient's body, a sensor, a transducer or the like (not shown). Moreover, the device 11 includes a front end 15 comprising analog front end circuitry 17 and a digital section 19. The front end 15 is connected to a back end unit 21 of the device 11.

The front end circuitry 17 comprises an analog filter 23, an input of which coupled with the input 13 and an output of which being connected to an analog-to-digital converter (ADC) 25 of the front end circuitry 17. In the shown example, the analog filter 23 is designed to function as an anti-aliasing filter. However, the analog filter may also be designed for different and/or additional purposes or even omitted completely. The ADC 25 is configured to convert the analog signal s applied to the input 13 and filtered by the analog filter 23 into a respective digital input signal x. The front end circuitry 17 is connected to an input of an adaptive digital filter 27 of the digital section 19 of the front end 15 so that the input signal x can be processed by the adaptive digital filter 27.

The adaptive digital filter 27 is configured to process (e.g. to filter) the input signal x, thereby generating an output signal y from the input signal x based on a set of filter coefficients $f_1, \ldots, f_k, \ldots, f_K$, where K denotes the number of filter coefficients. To this end, the adaptive digital filter 27 includes a filter block 29 that implements a digital filter according to a Finite Impulse Response (FIR) topology. Different types of filter topologies can be applied as well. The digital output signal y thus corresponds to a filtered signal generated by filtering the digital input signal x.

An output of the adaptive digital filter 27 of the digital section 19 is connected to the back end unit 21 of the measurement device 11 so that the output signal y is forwarded to the back end unit 21 when operating the measurement device 11. The back end unit 21 includes functions to process and/or analyze the output signal y representing the physiological parameter as needed by the considered application (e.g. ECG or EEG). Depending on the type of the measurement device, the back end unit 21 includes user interface devices for interacting with a human user (in particular to visualize the parameter represented by the output signal y) and/or communication circuitry to forward data related to the parameter represented by the output signal y to a computing system.

The adaptive digital filter 27 comprises a coefficient calculator 31 configured to calculate the filter coefficients $f_K$. In the shown example, the coefficient calculator 31 is adapted to calculate the set of coefficients $f_K$ repeatedly during the operation of the measurement device 11. For example, the coefficient calculator 31 can recalculate the set of filter coefficients $f_k$ periodically or in response to an event occurring within the measurement device 11.

Any suitable algorithm may be implemented in the coefficient calculator 31 for performing such adaptation operation. For example, an update algorithm can be implemented that re-calculates the set of filter coefficients $f_u$ based on the input signal x, the output signal y and the current set of filter coefficients $f_k$. In the shown example, the update algorithm implemented in block 31 applies an optimization method to minimize or maximize a metric of the output signal y, for example the deviation from a reference signal, time- or frequency-domain characteristics, or statistical metrics of the output signal y such as total variation, skewness, kurtosis or entropy. The metric (or any other type of target function) may be defined to measure the signal quality of the output signal to be optimized based on various aspects. One aspect, for example, may be a common mode component of the signal to be minimized. Further aspects of signal quality may be related to the presence or absence of frequency band within the signal, to a DC part of the signal or to numerical range limitation for saturation/overflow prevention.

The operation performed by the coefficient calculator 31 is thus an adaptation operation for generating a new set $f_k$ of filter coefficients, in particular an updated version of the current set of filter coefficients $f_k$. A result of this adaption operation includes the newly calculated set of filter coefficients $f_k$.

The digital section 19 of the front end 15 further includes an alarm constraint checker 33 configured for determining alarm information from the result of the adaptation operation. To this end, the constraint checker 33 applies an alarm constraint on the result of the adaptation operation in order to determine the alarm information. As illustrated in FIG. 1, the alarm information A may includes multiple alarm information elements $a_1, \ldots, a_N$ that are related to different alarm types. The individual alarm constraints may be predefined. For example an alarm constraint $C_1$ $(f_1, \ldots, f_K)$ based on the set of filter coefficients may be defined for determining a first alarm information element $a_1$. Further constraints $C_2, \ldots, C_N$ can be defined accordingly related to the other alarm information elements and alarm types. The alarm constraints define a set of values of at least a part of the result of the adaption operation. For example, the alarm constraint can define a set of values of the set of filter coefficients $f_1, \ldots, f_K$. As described below, the constraints can be defined using inequality equations related to a vector x including variables belonging to the result of the adaptation operation, e.g. $x=(f_1, \ldots, f_K)$.

An alarm generator 35 of the digital section 19 is configured to input the alarm information A and to generate at least one alarm based on the alarm information A. The alarm generator 35 is configured to generate alarms of a first class referred to as technical alarms CT based on the alarm information A. Technical alarms include alarm or failure conditions related to technical or physical aspects of the measurement process and are triggered if problems like an internal defect of the measurement device 11, defective cables connected to the input 13, defective electrodes sensors or transducers, the presence of significant interference, or poor or lost connection between the input 13 and the respective electrode/sensor transducer. The alarm generator 35 may be adapted to forward the technical alerts CT to the back end unit 21.

According to an extension of the example shown in FIG. 1, application-specific alarms CA can be generated by the alarm generator 35 additional to the technical alarms CT or instead of the technical alarms CT. The class of application-specific alarms CA refers to a predefined condition of a physiological parameter or process measured by the measurement device 11, e.g. "ventricular fibrillation" in an ECG.

Although the constraint checker 33 of the shown example operates on the set of filter coefficients $f_k$ repeatedly calculated by the coefficient calculator 31, it is possible to use other state information of the coefficient calculator 31 in addition to the filter coefficients $f_k$ or instead of the filter coefficients $f_k$. The internal state information is illustrated in FIG. 1 as dashed arrow labelled with $g_1$ and may include, for example, at least one slack variable when applying an optimization method in block 31.

The operations performed by the digital section 19 of the front end 15 are performed, at least in part, in software. In general, any combination of hardware and software can be used to implement the herein described functionality of the digital section 19. Accordingly, the measurement device 11, preferably the digital section 19, includes a programmable computer such a processing unit 37. The processing unit 37 includes at least one processor 39 operable to execute a computer program stored in a memory device 41 of the processing unit 37. The computer program is programmed to carry out at least some operations performed by the measurement device 11. Moreover, the program may be programmed to execute a method for operating the measurement device 11, which method will be described below in more detail. The processing unit 37 may be a general purpose computer, I/O circuitry of which being coupled with the remaining parts of the measurement device so that the herein described operations can be carried out.

Figure 2:
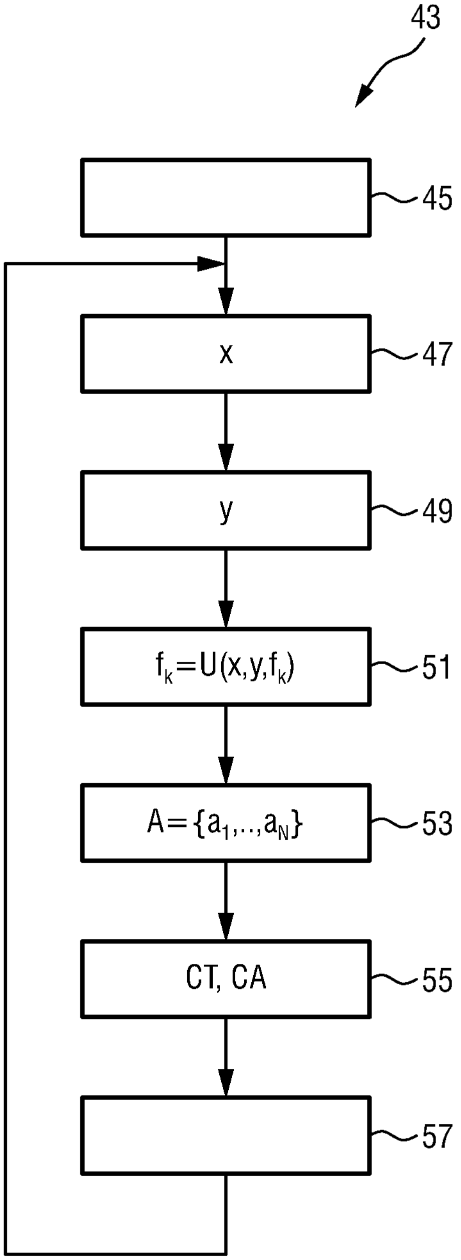
FIG. 2 shows a flow chart of a method for operating the physiological measurement device of FIG. 1.

FIG. 2 shows a method 43 for operating the physiological measurement device 11. After a start 45 of the method 43, a step 47 is performed for inputting the input signal x from the front end circuitry 17, the input signal x representing the analog signal s present at the input of the front end circuitry 17.

In a subsequent step 49, the output signal y is inputted, the output signal y corresponding to a filtered digital signal generated by the digital filter block 29 of the adaptive digital filter 27.

After inputting the signals x and/or y, the method 43 performs an adaptation operation 51 to calculate a new set of filter coefficients $f_k$ based on the input signal x, the output signal y and/or the current set of filter coefficients $f_k$. In other examples, where the input signal x or the output signal y are not needed by the adaption operation 51, the respective input operations 47 or 49 can be omitted.

The calculated set of filter coefficients $f_k$ belongs to a result of the adaptation operation performed in step 51. Step 53 executed after step 51 determines the alarm information A based on the result of the adaptation operation 51.

Finally, a step 55 of the method 43 generates at least one alarm based on the alarm information A. As explained above, depending on the concrete implementation, alarms of the technical class CT and/or the application-specific class CA may be supported.

Then, a step 57 is executed for waiting until a next iteration of the method 43 shall be performed by skipping back to step 47. Step 57 may trigger the next iteration based on a predefined delay and/or based on a predefined event that occurs within the measurement device 11. In particular step 57 may wait until a sufficient large number of samples of the input signal x and/or the output signal y are generated during the operation of the measurement device 11 and ready for being inputted.

Steps 47, 49, 51 and 57 are used in connection with measurement devices 11 that use adaptive filter technology in order to improve the quality of the signal y outputted by the front end 15. Steps 53 and 55, mainly including checking the result of the adaptation operation against the constraints, are dedicated to functionality of the measurement device 11 related to alarm generation and processing. As a consequence, the overhead caused by alarm generation is low compared to other approaches where the whole alarm detection and generation circuitry is built in parallel to the signal processing circuitry. Moreover, the alarms can be detected and generated independently from specific measurement processes, such as impedance measurement processes that require test signals to be applied to the input 13. The lack of test signals does not only simplify the design of the measurement device 11 but also reduces the likelihood of undesired interactions with other medical devices (not shown) that may be connected to the same person/patient as the present measurement device 11.

Figure 3:
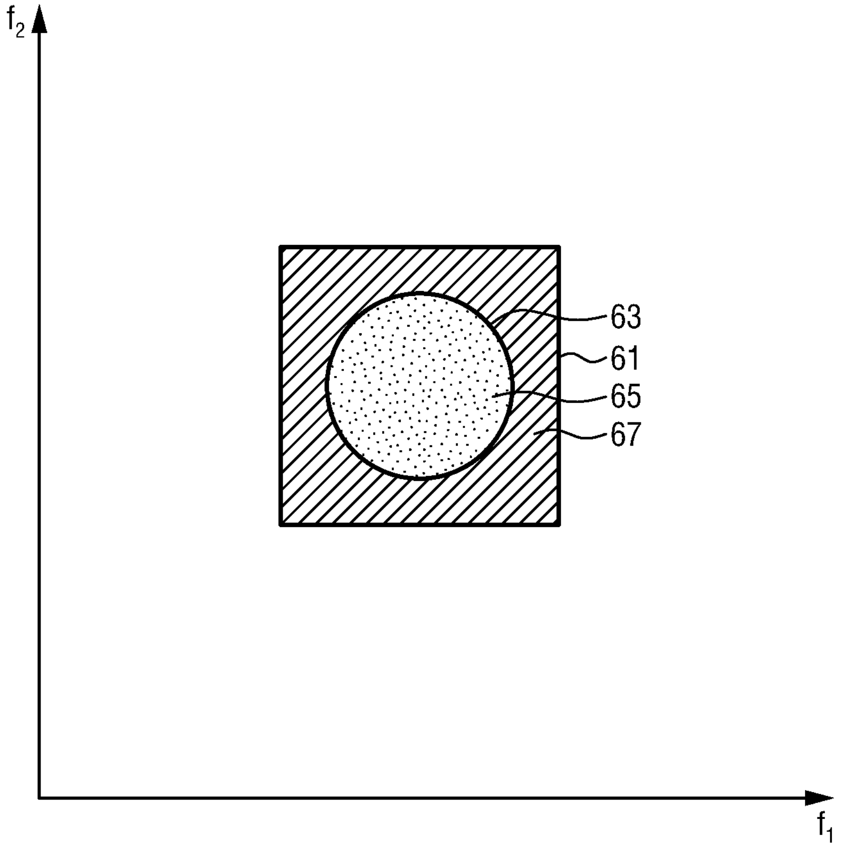
FIG. 3 shows an exemplary alarm constraint.

As shown in FIG. 3, an alarm constraint to be evaluated in step 53 and block 33 can be interpreted as a geometric region in a space defined by different variables of the result of the adaptation operation such as to filter coefficients $f_1$, $f_2$. For example, the digital adaptive filter 27 may constrain parameters, such as the filter coefficients, to a set of value constraints. Then, the alarm constraints are defined as a subset of the respective value constraints. The value constraints considered by the coefficient calculator 31 are illustrated as a rectangle 61. Valid solutions for the filter coefficients $f_1$, $f_2$ are located within the rectangle 61. The alarm constraint is limited by a circle 63. More specifically, the alarm constraint 63 requires that the filter coefficients $f_1$, $f_2$ must correspond to points located outside the circle 63. Accordingly, the dotted region 65 is referred to as a "good region" where the alarm information A does not indicate an alarm. A hatched area 67 outside the circle 65, however, corresponds to the alarm constraint and thus to an "alarm region" where the constraint check performed by block 33 and step 53 generates alarm information A indicating an alarm that is then processed by the alarm generator 35. FIG. 3 shows an example only. In general, the alarm constraint 63 should be selected such that it is a subset of the value constraint 61 applied by the coefficient calculator 31.

Figure 4:
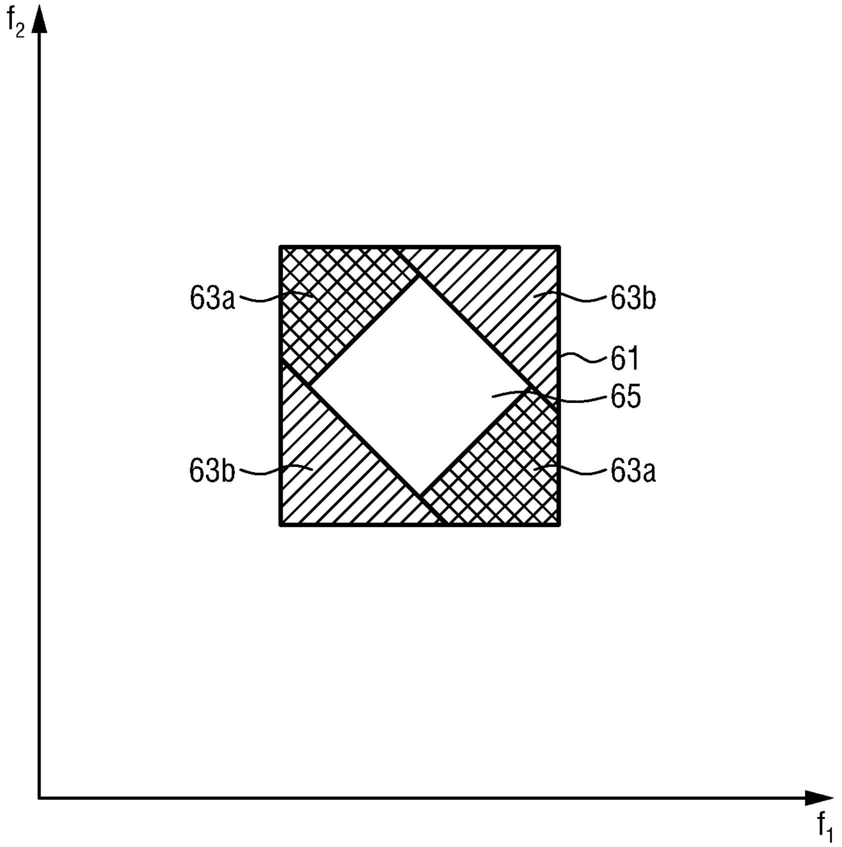
FIG. 4 shows a set of alarm constraints related to different types of alarms.

FIG. 4 shows an example where different alarm constraints 63*a*, 63*b* are defined related to different types of alarms. A first alarm constraint corresponds to the filter coefficients $f_1$, $f_2$ indicating a point within a checkered region 63*a*. A different region, illustrated as a hatched area 63*b* in FIG. 4, corresponds to a second alarm constraint. Filter coefficients $f_1$, $f_2$ corresponding to points located in the hatched area 63*b* correspond to a second alarm constraint. The area 65 located outside the two alarm constraints 63*a*, 63*b* but within the value constraint 61 correspond to the "good region". In the shown example, the first constraint defines an "electrode off" alarm (insufficient connection to an electrode) and corresponds to the region 63*a*. The second alarm constraint corresponds to an "interference alarm" (measurement device 11 and/or electrode, transducer, sensor, etc. subject to excessive interference) and to the hatched region 63*b*.

Other alarms may include "electrode quality low", "electrode off", "defective cable" and/or "defective device", etc.

Figure 5:
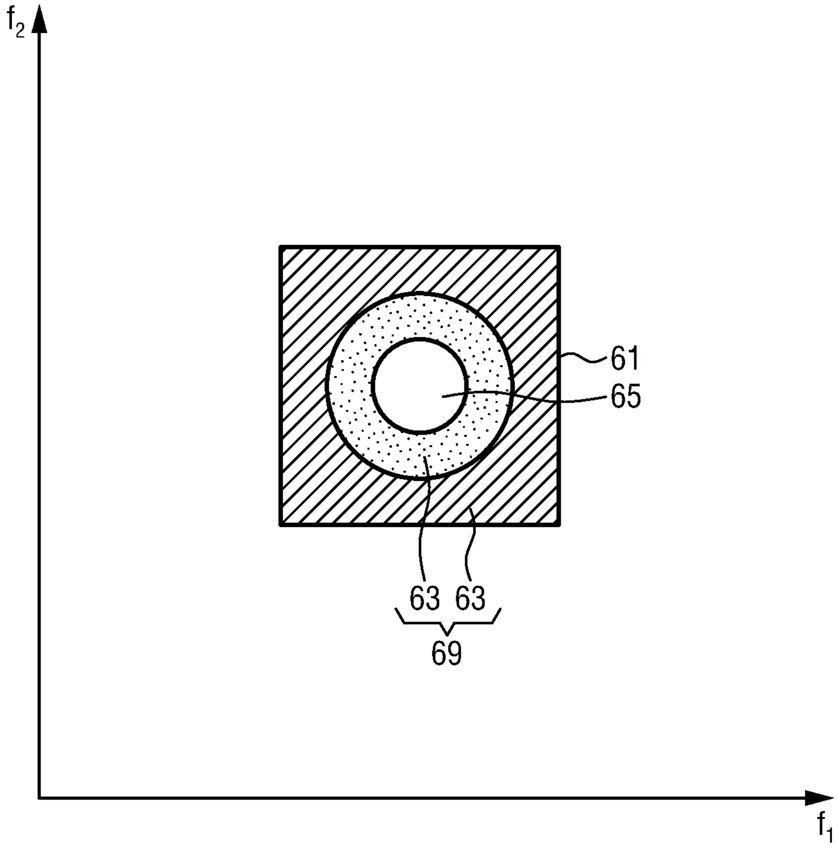
FIG. 5 shows a group of alarm constraints related to one alarm type but different severity levels related to this alarm type.

FIG. 5 shows an extension of the example of FIG. 3 where the respective alarm information element $a_i$ can have more than two different discrete values, whereas the alarm information generated according to the example of FIG. 3 is of a Boolean type (two different discrete values). As illustrated in FIG. 5, a group of alarm constraints are used for determining the respective alarm information. The different alarm constraints are associated with different severity levels of a certain type of alarm. In the shown example, two alarm constraints 63 belong to a group 69 of alarm constraints. Respective areas correspond to "yellow region" (dotted ring-shaped region) and a "red region" (dashed with solid lines). The good region 65 corresponds to the white circular disk located in the center of FIG. 5. In this context, the good region 65 is also referred to as "green region". "Green", "yellow", "red" are related to increasing severity levels of the alarm. Alarms that have alarm information element that can have more than two discrete values may be used to indicate an electrode quality so that more than two levels of electrode quality can be determined.

The example of FIG. 4 showing multiple types of alarms can be extended in the same way by assigning a group of alarm constraints to at least one alarm type.

In general, the alarm constraints of one group of alarm constraints should be so defined that starting from a first alarm constraint (e.g. yellow region) of the group, each subsequent alarm constraint of a certain alarm constraint of the group is a superset of that alarm constraint. The respective subsequent alarm constraint corresponds to a higher severity level. As shown in FIG. 5, the alarm constraint corresponding to the highest severity level may be identical to the value constraint 61.

Figure 6:
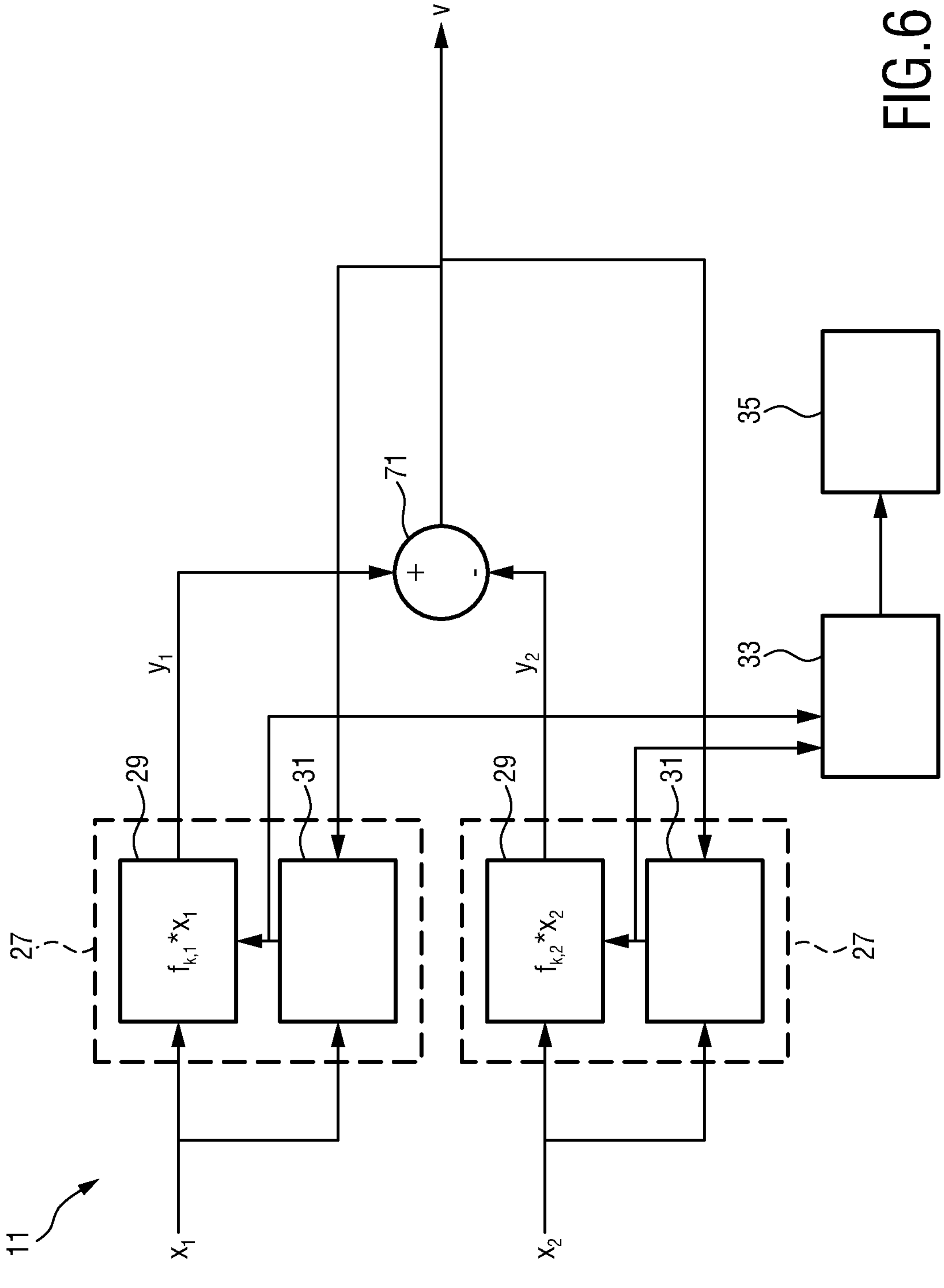
FIG. 6 shows a signal flow diagram of a physiological measurement device comprising multiple digital filters associated with different channels.

As shown in FIG. 6, the principle of the present disclosure can also be applied in connection with measurement devices 11 that have multiple channels. The shown example has two channels. Accordingly there are two analog signals $s_1$, $s_2$ (not shown), two respective digital input signals $x_1$, $x_2$ and two respective output signals $y_1$, y2 being filtered signals. The subtractor 71 of the digital section 19 is configured to subtract the second output signal $y_2$ from the first output signal $y_1$ so that a differential measurement can be performed and a respective vector signal v is output by the subtractor 71. Moreover, multiple digital filters 27 are implemented, each of them assigned to a specific input signal $x_1$, $x_2$. The result of the adaptation operation to be considered by the alarm constraint checker 33 includes results of adaptation operations performed by the coefficient calculators 31 of the individual adaptive digital filters. The alarm constraint checker 33 is configured to perform joint alarm constraint checks, i.e. to check the adaption operation results (e.g. sets of filter coefficients $f_{k,1}$, $f_{k,2}$) of multiple coefficient calculators 31 being part of different adaptive digital filters 27 against respective alarm constraints.

Although illustrated in the above examples in the form of two dimensional diagrams, in practical implementation the value constraints and the alarm constraints can be expressed as inequalities of matrix equations or vector norms of matrix equations. Calculations based on these expression (e.g. inequalities of matrix equations) can be implemented in the constraint checker 33 and in respective method step 53. The equations may be linear equations, polynomial equations or other types of non-linear equations. It is also possible to express the value and/or alarm constraints in an algorithmic form should the equation based formulation be unsuitable and implement the constraint checker 33 and the respective method step 53 based on the algorithmic form.

When using linear equations, the general forms for the vector x containing the parameters, e.g. the set(s) of filter coefficients, of the adaptive filter are $$c^T x + d \leq 0$$

$$\|Ax+b\|+d \leq 0$$

$$\|Ax+b\|+d \geq 0$$

Depending on the choice of the matrix A, the vectors b and c, the scalar d and vector norm $\|\cdot\|$, e.g. Euclidean (l2) norm, Manhattan (l1) norm, maximum (l∞) norm) a wide variety of constraint types can be formulated.

The above formal specification of constraints can be applied for both defining the value constraints used for calculating updated set(s) of filter coefficients as well as for defining the alarm constraint applied by the constraint checker 33 and method step 53. However, each alarm constraint is a subset of the value constraint; in other words, the set of values x allowed according to each alarm constraint is a subset of the values x allowed according to the value constraint. This subset relationship is also illustrated in the diagrams of FIGS. 3 to 5. All alarm constrains are shown as regions that are located within the area surrounded by rectangle 61 corresponding to the respective value constraint.

Some examples are given below.

$1^T x - d \leq 0$: Constrain the sum of the coefficients (which is the gain at f=0 Hz) to be less than d.

$-1^T x + d \leq 0$: Constrain the gain at f=0 Hz to be greater than d.

$\|x - x_0\| - d \leq 0$: Constrain the distance of x from a reference, initial or default point $x_0$ to at most d.

The last example is especially useful if the value of x is known for the ideal case and used as the initial value x0 of filter coefficients. The scalar c can be interpreted as the maximum distance from the ideal case that the adaptive filter coefficients may reach without triggering an alarm.

To sum up, the measurement devices 11 described herein include means for generating technical alarms or even application-specific alarm in the measurement device that include adaptive filters as part of their signal processing chain. In other words, the parts 33, 35 and steps 53 and 55 dedicated for generating and processing alarms rely on functions, such as updating the filter coefficients in block 31 and step 51, which are needed for processing the measured signal anyway. As a consequence, generation and handling of the errors can be implemented simply and efficiently.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A physiological measurement device comprising a processor configured to input at least one digital signal (x) from frontend circuitry of the measurement device, the digital signal (x) representing an analog signal(s) present at an input of the frontend circuitry and at least one filtered digital signal (y), the filtered digital signal (y) generated by at least one digital filter from the digital signal (x) based on a set of filter coefficients (f·sub·k);

a coefficient calculator configured to perform an adaptation operation based on the digital signal (x) and the filtered digital signal (y), wherein the adaptation operation is subject to at least one value constraint related to a filter coefficient (f·sub·k); and a checker configured to determine alarm information (A) from a result (f·sub·k, g·sub·1) of the adaptation operation, wherein the checker is a constraint checker operating based on at least one constraint defined for at least one variable of the result of the adaptation operation, wherein determining the alarm information comprises checking at least one alarm constraint against the result of the adaptation operation, the at least one alarm constraint being a subset of the at least one value constraint, and wherein the alarm information (A) comprises multiple alarm information elements (a·sub·1, . . . , a·sub·N) related to different alarm types, a specific alarm constraint being assigned to each of these alarm information elements.

2. The device of claim 1, wherein the result of the adaptation operation includes an updated set of filter coefficients (f·sub·k) and determining the alarm information is based on the updated set of filter coefficients (f·sub·k).

3. The device of claim 2, wherein determining the alarm information is based on at least one alarm constraint applicable to at least one filter coefficient (f·sub·k) of the set of filter coefficients.

4. The device of claim 3, wherein the adaptation operation is subject to at least one value constraint related to a filter coefficient (f·sub·k) and the alarm constraint is a subset of the value constraint.

5. The device of claim 1, wherein the alarm type includes a technical alarm (CT) and/or an application specific alarm (AI).

6. The device of claim 1, wherein determining the alarm information is based on at least one group of alarm constraints, the alarm constraints of the group of alarm constraints being associated with different severity levels of a certain type of alarm.

7. The device of claim 6, wherein the alarm constraints of the group of alarm constraints can be sorted so that, starting from a first alarm constraint of the group, each subsequent alarm constraint of a certain alarm constraint of the group is a superset of that certain alarm constraint, the subsequent alarm constraint corresponding to a higher severity level than the certain alarm constraint.

8. The device of claim 1, wherein the result of the adaptation operation comprises a plurality of sets of filter coefficients (f·sub·k,1, f·sub·k,2) related to multiple digital filters and multiple alarm constraints, each of the alarm constraints applicable to a different set of the plurality of sets of filter coefficients.

9. The device of claim 1, wherein performing the adaptation operation comprises solving an optimization problem.

10. A method for operating a physiological measurement device, the method comprising inputting at least one digital signal (x) from frontend circuitry of the measurement device, the digital signal (x) representing an analog signal(s) present at an input of the frontend circuitry; inputting at least one filtered digital signal (y) generated by at least one digital filter from the digital signal (x) based on a set of filter coefficients; performing an adaptation operation based on the digital signal (x) and the filtered digital signal (y), wherein the adaptation operation is subject to at least one value constraint related to a filter coefficient; and determining alarm information from a result (f·sub·k, g·sub·1) of the adaptation operation, wherein determining the alarm information comprises checking at least one alarm constraint against the result of the adaptation operation, the at least one alarm constraint being a subset of the at least one value constraint, generating alarm information (A) that comprises multiple alarm information elements (a·sub·1, . . . , a·sub·N) related to different alarm types, and assigning a specific alarm constraint to each of these alarm information elements.

11. A non-transitory computer medium that stores therein a computer program product, which, when executed on a processor, causes the processor to carry out the steps of the method as claimed in claim 10 to be performed.

* * * * *